Figure 1:
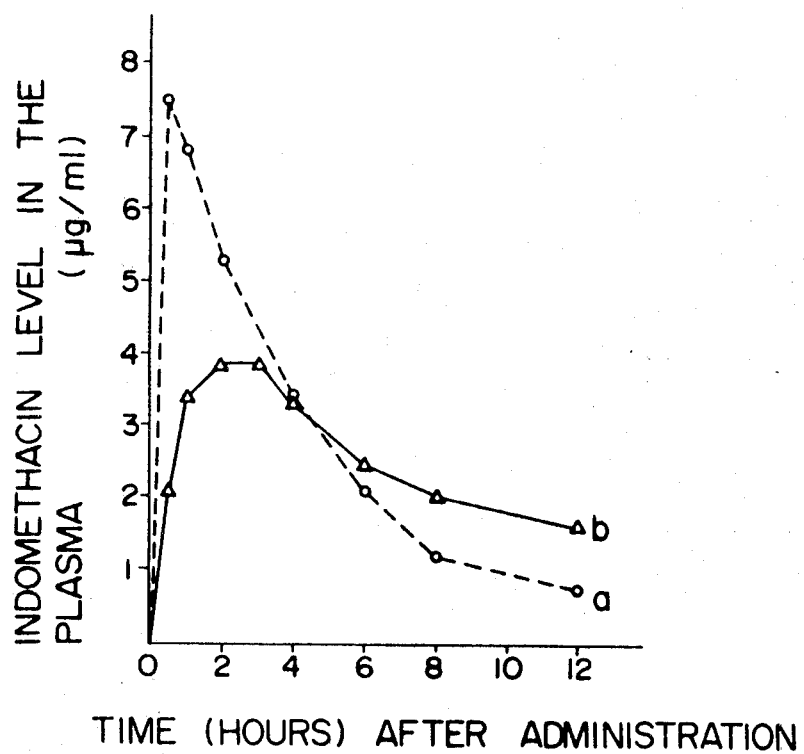

United States Patent [19]

Nagai et al.

[11] 4,250,163
[45] Feb. 10, 1981

[54] METHOD AND PREPARATION FOR ADMINISTRATION TO THE MUCOSA OF THE ORAL OR NASAL CAVITY

[75] Inventors: Tsuneji Nagai, Chofu; Yoshiharu Machida, Kawasaki; Yoshiki Suzuki; Hiroshi Ikura, both of Hino, all of Japan

[73] Assignee: Teijin Limited, Japan

[21] Appl. No.: 103,558

[22] Filed: Dec. 13, 1979

Related U.S. Application Data

[62] Division of Ser. No. 17,059, Mar. 2, 1979.

[51] Int. Cl.³ .................... A61K 31/74; A61K 31/78
[52] U.S. Cl. .................................. 424/14; 106/35;
128/260; 424/16; 424/19; 424/22; 424/28;
424/78; 424/81
[58] Field of Search ............... 424/14, 16, 19, 22,
424/28, 78, 81; 106/35; 128/260

[56] References Cited

U.S. PATENT DOCUMENTS

| | | | |
|---|---|---|---|
| 2,997,399 | 8/1961 | Eborhard et al. | 106/35 |
| 3,440,065 | 4/1969 | La Via | 106/35 |
| 3,511,791 | 5/1970 | Puetzer et al. | 106/35 X |
| 3,833,518 | 9/1974 | Rubin et al. | 106/35 X |
| 3,868,259 | 2/1975 | Keegan et al. | 106/35 X |
| 3,868,432 | 2/1975 | Keegan et al. | 106/35 X |
| 4,059,686 | 11/1977 | Tanaka et al. | 424/19 |

FOREIGN PATENT DOCUMENTS 51-38412 3/1976 Japan.
53-130421 11/1978 Japan.

Primary Examiner—Shep K. Rose
Attorney, Agent, or Firm—Wenderoth, Lind & Ponack

[57] ABSTRACT

A method for administering a medicament which comprises adhering to the mucosa of the oral or nasal cavity a pharmaceutical preparation comprising (a) a water-swellable and mucosa-adhesive polymeric matrix comprising about 50 to about 95% by weight of a cellulose ether and about 50 to about 5% by weight of a homo- or copolymer of acrylic acid or a pharmaceutically acceptable salt thereof, and (b) dispersed therein, a pharmaceutically effective amount of the medicament, said preparation releasing continuously the medicament at a controlled rate; and causing the released medicament to be absorbed through the mucosa or enterally; said mucosa-adhesive preparation; and process for said preparation.

9 Claims, 3 Drawing Figures

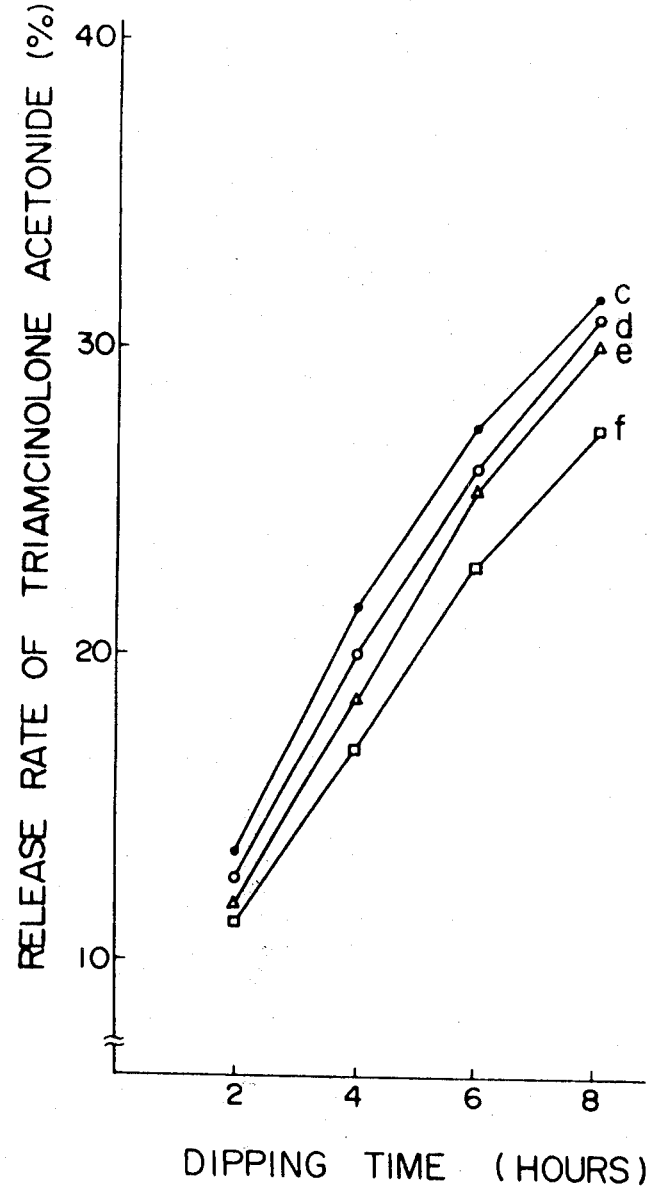

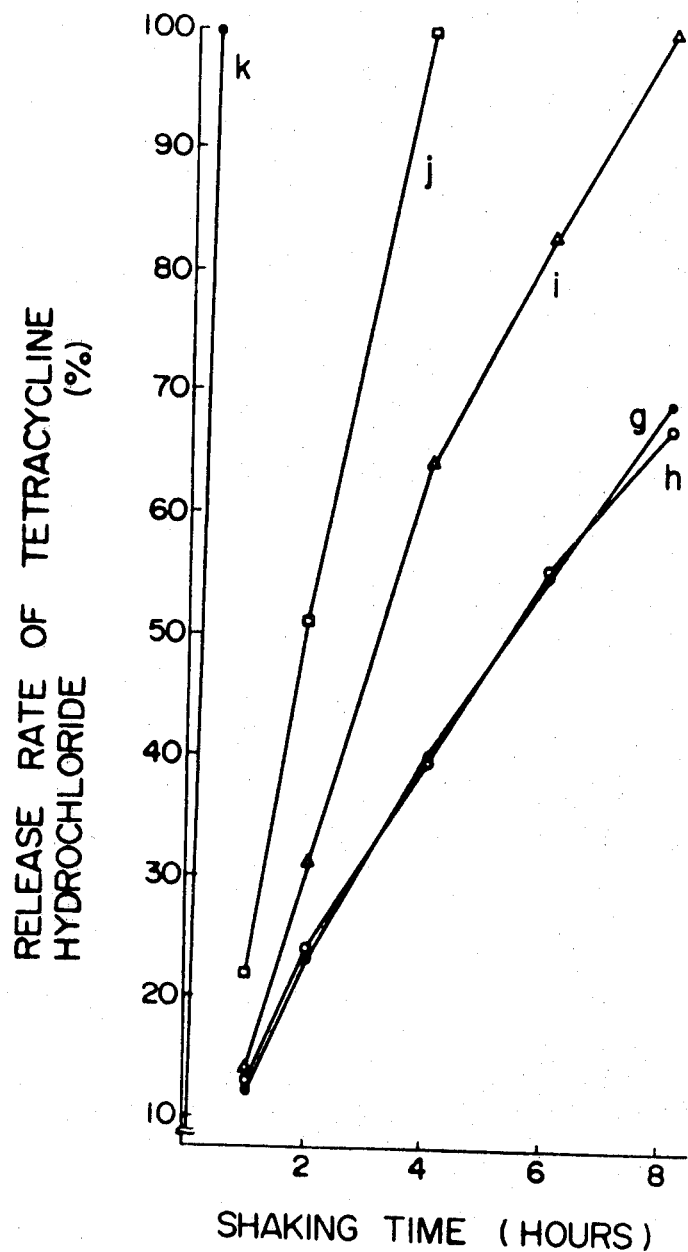

METHOD AND PREPARATION FOR ADMINISTRATION TO THE MUCOSA OF THE ORAL OR NASAL CAVITY

This is a division of application Ser. No. 17,059, filed Mar. 2, 1979.

This invention relates to a method of administering a mucosa-adhesive preparation by causing it to adhere to the mucosa of the oral or nasal cavity, to the use of said mucosa-adhesive preparation for administration in adherence to the mucosa of the oral or nasal cavity, to said mucosa-adhesive preparation, and to a process for preparing said preparation.

More specifically, this invention relates to a method for administering a medicament for the prevention, curing and treatment of a disease, which comprises adhering to the mucosa of the oral or nasal cavity a slow-releasing preparation which adheres to the mucosa of the oral or nasal cavity wetted with the saliva or the intranasal secretion and gradually releases the medicament contained therein while gradually swelling upon the absorption of the saliva or the intranasal secretion; and causing the released medicament to be absorbed through the mucosa or enterally. It also pertains to said preparation and a process for preparing said preparation.

Various suggestions have been made as to "slow-releasing" pharmaceutical preparations for internal administration which gradually release medicaments contained therein to maintain the efficacy of the medicaments over long periods of time.

On the other hand, buccal tablets, troches, sublingual tablets, ointments for the oral cavity, nose drops, and sprays are known as preparations for administration to the oral or nasal cavity. However, the conventional buccal agents, troches and sublingual tablets are difficult to retain in the oral cavity for long periods of time, and the patients frequently chew and swallow them. Ointments for the oral cavity are known which contain a mixture of beeswax of plastibase with gelatin, pectin or sodium carboxymethyl cellulose. However, they adhere only insufficiently to the mucosa of the oral cavity and cannot be held there for long periods of time. With the nose drops and sprays, it is difficult to hold the medicament in the nasal cavity for long periods of time. Accordingly, none of these pharmaceutical preparations are entirely satisfactory in slowly releasing the medicaments and maintaining their efficacy for long periods of time.

Japanese Laid-Open Patent Publication No. 38412/76 discloses a buccal preparation composed of a medicament, a sodium salt of polyacrylate, and an excipient (i.e., crystalline cellulose, mannitol, lactose, sorbitol, anhydrous calcium phosphate, amylose), and a process for making said preparation. It is stated that this preparation is characterized by the fact that it adheres to a particular site upon absorption of moisture by the sodium salt of polyacrylate, then swells, and gradually dissolves at the site over a long period of time whereby the medicament comes out almost uniformly. Experiments of the present inventors have shown however that the preparation disclosed in Japanese Laid-Open Patent Publication No. 38412/76 does not sufficiently adhere to the mucosa of the oral cavity, and since it becomes flowable as a result of swelling and dissolution in the oral cavity, it has poor form retention and is sticky; and therefore that the slow releasing effect of the medicament over a long period of time is not entirely sufficient and it also gives an unpleasant feeling to the subject.

As a slow releasing preparation other than those for administration to the oral cavity, Japanese Laid-Open Patent Publication No. 130421/78 discloses a preparation for treatment of uterine cancer comprising a carcinostatic agent, hydroxypropyl cellulose and polyacrylic acid or its pharmaceutically acceptable salt, and a process for preparing said preparation. This preparation is characterized by the fact that since it is intended for administration to the vagina or uterus, its adhesion to the site of cancer tissues within the vagina or uterus and its form retention are good, and the penetration of the medicament into that site is good with reduced side-effects, such as irritation or erosion, on the healthy vaginal mucosa. For example, Example 6 of Japanese Laid-Open Patent Publication No. 130421/78 which describes clinical data shows that a preparation obtained by blending bleomycin hydrochloride, a therapeutic agent for treating squamous cell carcinoma, with a 1:2 polymer mixture of hydroxypropyl cellulose and polyacrylic acid produced a therapeutic effect when it was caused to adhere to the cervix uteri of a patient with cancer at cervix uteri in the 0 stage or Ia stage. This preparation is an excellent slow-releasing preparation because it adheres to the mucosa of the cervix uteri and releases the medicament directly to the cancerous site over long periods of time without detrimental side-effects. Japanese Laid-Open Patent Publication No. 130421/78, however, gives no suggestion as to whether this preparation could be used for administration to the mucosa of the oral or nasal cavity. It is well known that the vagina or uterus differs from the oral or nasal cavity not only in structure and function and reactivity to external stimulation, but also in the quality and quantity of secretions, the motion of the mucosa and its extent. As far as the present inventors know, there is no prior example of applying a matrix of a vaginal suppository directly to a preparation for administration to the oral or nasal cavity. Furthermore, as will be described in detail hereinbelow, when the preparation containing a 1:2 mixture of hydroxypropyl cellulose and polyacrylic acid as described in Japanese Laid-Open Patent Publication No. 130421/78 was caused to adhere to the mucosa of the oral cavity, whitening or the occurrence of blister-like projections is seen in the mucosa, thus showing strong irritation to the mucosa.

It is an object of this invention therefore to provide a method for administering a medicament which comprises adhering to the mucosa of the oral or nasal cavity a preparation having a specified matrix composition and being adhesive to the mucosa of the oral or nasal cavity, and releasing the medicament continuously and slowly at a controlled rate.

Another object of this invention is to provide a method of using said preparation for continuous slow-releasing adminstration.

Still another object of this invention is to provide a preparation suitable for the prevention, curing and treatment of a disease as a result of adhering to the mucosa of the oral or nasal cavity and gradually releasing the medicament contained therein.

Yet another object of this invention is to provide a method for producing the preparation of this invention.

Further objects and advantages of the invention will become apparent from the following description.

According to this invention, the above objects and advantages can be achieved by a method for administering a medicament which comprises adhering to the mucosa of the oral cavity or nasal cavity a pharmaceutical preparation comprising
  (a) a water-swellable and mucose-adhesive polymeric matrix comprising about 50 to about 95% by weight of a cellulose ether and about 50 to about 5% by weight of a homo- or copolymer of acrylic acid or a pharmaceutically acceptable salt thereof, and
  (b) dispersed therein, a pharmaceutically effective amount of the medicament.
said preparation releasing the medicament continuously at a controlled rate; and causing the released medicament to be absorbed through the mucosa or enterally.

The pharmaceutical preparation used in the method of administration in accordance with this invention forms part of the present invention. It comprises
  (a) a water-swellable and mucosa adhesive polymeric matrix comprising about 50 to about 95% by weight of a cellulose ether and about 50 to about 5% by weight of a homo- or copolymer of acrylic acid or a pharmaceutically acceptable salt thereof, and
  (b) dispersed therein, a pharmaceutically effective amount of a medicament,
and slowly releases the medicament while adhering to the mucosa of the oral or nasal cavity stably for long periods of time.

Accordingly, the above objects and advantages of this invention are similarly achieved by use of said pharmaceutical preparation comprising a matrix composed of components (a) and (b) for the administration of said medicament.

According to the administering method of this invention, a medicament to be administered is used as a pharmaceutical preparation adhering to the mucosa of the oral or nasal cavity. If the method is taken as a method of whole body administration for the prevention, curing and treatment of a disease, not only can an effect by the slow release of the medicament be expected, but also because of the direct absorption of the medicament through the mucosa of the oral or nasal cavity, safe administration of a medicament, such as indomethacin, which tends to cause ulcer to the wall of the gastrointestinal organs can be effected, and such a medicament as insulin which easily decomposes in the stomach and intestines and is little effective by oral administration can be expected to be administered by means other than injection. If the administering method of this invention is taken as a method of topical administration for the prevention, curing and treatment of a disease within the oral or nasal cavity, it has the advantage that because the medicament can be administered directly to the infected part over a long period of time, the disease can be prevented, cured or treated with exact results using a small amount of the medicament.

The administering method of this invention also has the advantage that the residence time in the stomach and intestines is not restricted as is seen with conventional slow-releasing pharmaceutical preparations for oral administration which are in the form of capsules and the like, and the exact slow-releasing effect of the medicament can be expected, and a sudden change in body condition which may be caused by the administration of the medicament can be dealt with easily by simply removing the pharmaceutical preparation from the oral or nasal mucosa.

When the cellulose ether and polyacrylic acid or its pharmaceutically acceptable salt are used singly in producing a pharmaceutical preparation, the resulting preparation is unsuitable as a slow-releasing preparation because it does not adhere to the mucosa of the oral or nasal cavity or even when it adheres, it is relatively rapidly disintegrated, dispersed or dissolved by the saliva or other secretions. In contrast, the pharmaceutical preparation of this invention containing a mixture of these in a specified ratio has sufficient adhesion to the mucosa, and does not dissolve, flow out and get out of shape although it is swollen and softened with the saliva or secretions. Moreover, the preparation in accordance with this invention does not irritate the mucosa of the oral or nasal cavity, and releases the medicament uniformly over a long period of time either topically or through the entire body. These properties and activities make it excellent for application to the oral or nasal cavity as a slow-releasing preparation.

The water-swellable and mucosa-adhesive polymeric matrix in the present invention is composed of the cellulose ether and polyacrylic acid or its pharmaceutically acceptable salt in the above-specified ratio, and makes the slow-releasing pharmaceutical preparation of this invention surely adhesive to the oral or nasal mucosa.

A pharmaceutically effective amount of a medicament is uniformly dispersed in the polymeric matrix, and the matrix consists of about 50 to about 95% by weight of the cellulose ether and about 50 to about 5% by weight of polyacrylic acid or its pharmaceutically acceptable salt.

The specified ratio of the two polymers which form the polymeric matrix is essentially required in order for the slow-releasing preparation of this invention not to cause whitening or blisters to the mucosa of the oral or nasal cavity, and also to release the medicament at a controlled rate.

When the amount of the acrylic acid polymer or its pharmaceutically acceptable salt is more than about 50% by weight, the pharmaceutical preparation irritates the mucosa of the oral or nasal cavity, and tends to cause marked whitening of the mucosa and the marked occurrence of blisters therein.

Preferably, the polymeric matrix used in this invention consists of about 65 to about 90% by weight of the cellulose ether and about 35 to about 10% by weight of the polyacrylic acid or its pharmaceutically acceptable salt.

The cellulose ether used in this invention is a cellulose derivative resulting from the partial or whole etherification of a plurality of hydroxyl groups of cellulose, and includes, for example, lower alkyl ethers, hydroxy lower alkyl ether, and carboxy lower alkyl ethers of cellulose. The ether groups need not to be of a single kind, and there may be also used cellulose ethers which intramolecularly contain two or more ether groups, for example both lower alkyl groups and hydroxy lower alkyl groups. Of these, lower alkyl ethers or hydroxy lower alkyl ethers of cellulose are used preferably. The "lower alkyl groups", as used herein, denote alkyl groups containing not more than 5 carbon atoms, preferably not more than 3 carbon atoms.

Examples of these cellulose ethers include methyl cellulose, ethyl cellulose, propyl cellulose, hydroxyethyl cellulose, hydroxypropyl cellulose, carboxymethyl cellulose, carboxyethyl cellulose and carboxymethyl hydroxyethyl cellulose. Of these, methyl cellulose, hydroxyethyl cellulose, hydroxypropyl methyl cellulose and hydroxypropyl cellulose are preferred, the hydroxypropyl cellulose being especially preferred.

These cellulose ethers may be used singly or as a mixture of two or more.

The molecular weight and the degree of ether substitution of the cellulose ether are not critical, and all commercially available products can be used in this invention.

Preferably, the cellulose ether used in this invention has a viscosity, determined for its 2% by weight aqueous solution of 20° C., of 3 to 100,000 centipoises, more preferably 3 to 10,000 centipoises, especially preferably 6 to 6,000 centipoises.

Furthermore, the cellulose ether used in this invention has an ether substitution degree of preferably 0.1 to 6.0, more preferably 0.4 to 4.6.

The degree of ether substitution denotes the average number of ether groups for three hydroxyl groups per glucose unit constituting the cellulose.

The copolymer of acrylic acid used in this invention denotes a copolymer derived from acrylic acid and allyl sucrose, methyl acrylate, methacrylic acid, methyl methacrylate, hydroxyethyl methacrylate, styrene or a vinyl-type ether monomer such as methyl vinyl ether.

The ratio of the comonomer can be varied within the range in which the copolymer is maintained water-soluble or water-swellable, and is limited to the range in which the pharmaceutical preparation of this invention is maintained adhesive to the mucosa of the oral or nasal cavity or non-irritating. It is generally not more than about 20 mole % based on the copolymer.

A mixture of the homo- or copolymer of acrylic acid readily available on the market with a minor amount (usually, not more than about 20% by weight) of another water-soluble polymer (such as a homo- or copolymer of methacrylic acid or its salt, or polyethylene glycol) can also be used as the acrylic acid homo- or copolymer in this invention.

Suitable pharmaceutically acceptable salts of the acrylic acid homo- or copolymer include alkali metal salts such as sodium or potassium salt and ammonium salts. The degree of neutralizing of the salts is not limited. The acrylic acid homo- or copolymer or its pharmaceutically acceptable salts may have any molecular weight. Desirably, they have a viscosity, measured at 25.0° ±0.5° C. for an aqueous solution of a sodium salt thereof having a pH of 7 to 7.5 and a concentration of 0.2% by weight as the acrylic acid homo- or copolymer, of generally 360 to 165,000 centipoises, preferably 3,600 to 16,500 centipoises.

The homo- or copolymers of acrylic acid or pharmaceutically acceptable salts thereof in this invention may be used singly or as a mixture of two or more.

The pharmaceutical preparation of this invention contains a medicament for the prevention, curing or treatment of a disease uniformly dispersed in the polymeric matrix consisting of the homo- or copolymer acrylic acid or its pharmaceutically acceptable salt and the above mentioned cellulose ethers.

Such a medicament is selected by those skilled in the art according to the disease to which the pharmaceutical preparation is to be applied. Examples include analgesic and anti-inflammatory agents such as acetaminophen, phenacetin, aspirin, aminopyrine, sulpyrine, phenylbutazone, mefenamic acid, flufenamic acid, Ibufenac, Ibuprofen, indomethacin, colchicine, and Probenecid; anti-inflammatory enzymes such as $\alpha$-chymotryprin; anti-inflammatory steroids such as hydrocortisone, prednison, prednisolone, triamcinolone, dexamethasone and betamethasone; antihistamines such as diphenhydramine hydrochloride and dexchlorpheniramine maleate; antibiotics or fungicides such as tetracycline hydrochloride, leucomycin, fradiomycin, penicillin and its derivatives, cephalosporin derivatives and erythromycin; chemotherapeutic agents such as sulfathiazole and nitrofurazone; topical anaesthetics such as benzocaine; cardiac tonics such as digitalis and digoxin; vasolilators such as nitroglycerin and papavarine hydrochloride; antitussives and expectorants such as codeine phosphate and isoproterenol hydrochloride; oral antiseptics such as chlor hexidine hydrochloride, hexylresorcinol, dequalinium chloride and ethacridine; drugs for the digestive organs such as pepstatin, azulene, phenovalin and vitamin U; enzymes such as lysozyme hydrochloride and dextranase; hypoglycemics such as insulin; and other drugs including hemostats, sex hormones, hypotensives, sedatives, anti-tumor agents and antacids.

There drugs can be used either singly or as a mix mixture of two or more. The amount of the medicament to be blended with the polymeric matrix is the one sufficient to prevent, cure or treat a disease to which the pharmaceutical preparation of this invention is to be applied.

The slow-releasing pharmaceutical preparation, in addition to the polymeric matrix and the medicament dispersed therein, may further contain at least one known excipients such as lubricants, binders, vehicles, coloring agents, taste controlling agents and odor controlling agents as required for improving the appearance, odor or taste of the pharmaceutical preparation. The lubricants include talc, stearic acid, stearate salts, and waxes. Example of the binders include starch, dextrin, tragacanth, gelatin, polyvinyl pyrrolidone and polyvinyl alcohol. The vehicles include starch, crystalline cellulose, dextrin, lactose, mannitol, sorbitol, and anhydrous calcium phosphate. The agents for controlling tastes and smell are citric acid, fumaric acid, tartaric acid, menthol, and citrus perfumes.

The pharmaceutical preparation of this invention can be prepared by dispersing a pharmaceutically effective amount of a medicament in the water-swellable and mucosa-adhesive polymeric matrix comprising about 50 to about 95% by weight of a cellulose ether and about 50 to about 5% by weight of a homo- or copolymer of acrylic acid or its pharmaceutically acceptable salt.

In practice, the medicament is fully mixed with the cellulose ether and the homo- or copolymer of acrylic acid or its pharmaceutically acceptable salt, and if desired, at least one of lubricants, binders, vehicles, coloring agents, taste or smell controlling agents, etc. is added to form an intimate mixture. Then, as required, the mixture is molded in a known manner into the desired form. The intimate mixture means that the constituent ingredients in the pharmaceutical preparation are mixed as uniformly as possible so that none of the ingredients are localized. Usually, it is preferred to mix these ingredients in fine powder form.

Examples of the form of the preparation are tablets, granules, fine granules, powders or fillings such as a dental cone. The tablets are produced by press-forming with a punch, die or press a suitable amount of a mixture of the individual ingredients either as such or after press-forming and granulating it. The granules and fine granules are produced by press-forming the mixture of the individual ingredients, pulverizing the mixture and sieving the pulverized particles. The powders are produced by pulverizing the press-formed mixture to a fine powder form, or mixing the individual components in fine powder form.

The pharmaceutical preparation of this invention contains a pharmaceutically effective amount of a medicament. The amount differs from medicament to medicament, and is determined according to the age, sex, condition, etc. of the patient. The number of administrations may be 1 to 5 per day, and usually, by one administration, the pharmaceutical preparation can be easily held in the oral or nasal cavity for 4 hours even when the patient is in action.

Administration of the pharmaceutical preparation of this invention may be to any part of the mucosa of the oral or nasal cavity.

When a topical disease in the oral cavity or nasal cavity is to be treated, it is preferred to apply the pharmaceutical preparation to the mucosa in a manner to cover the infected site.

When the disease extends over a relatively broad area within the oral cavity or nasal cavity, or when absorption of the medicament from a board area of the mucosa is desired, the pharmaceutical preparation in the form of granules, fine granules or powders is sprinkled onto the infected site or the mucosa or sprayed onto such a part by a suitable device. Some medicaments are desired to be highly absorbed through the buccal mucosa, the sublingual mucosa and the nasal mucosa. In such a case, it is possible to apply the pharmaceutical preparation directly to such a site by means of pincers or by holding it with fingers to maintain it adhering thereto for a long period of time.

Generally, the nasal mucosa is more sensitive to irritation, yields less secretion and permits better absorption of a medicament than the oral mucosa. Accordingly, it is possible to employ an administering method which is expected to produce a greater therapeutic effect by utilizing such an inherent nature of the nasal mucosa.

The slow-releasing pharmaceutical preparation of this invention which is adhesive to the mucosa of the oral or nasal cavity, the method for its administration, and the method for its use exhibit the following excellent results.

(1) The slow-releasing preparation of this invention adheres to a particular site upon absorption of the saliva or secretions, and even in the swollen stage, shows very good adhesion to that site. Thus, a medicament can be caused to act in a high concentration directly and locally on a diseased site or a site of absorption within, and in the neighborhood of, the oral or nasal cavity. The pharmaceutical preparation itself does not pass the site where a medicament is to be absorbed or acted upon, whereas slow-releasing capsules for oral administration do.

(2) The slow-releasing preparation of this invention swells upon absorption of the saliva or secretions, and gradually releases the medicament at a controlled rate. The preparation swells by the saliva or secretions, and releasing of the medicament starts at the swollen part of the preparation. Thus, according to the administering method of this invention, the medicament can be continuously administered to the diseased site or the site of absorption over a long period of time.

For example, the present inventors prepared tablets of a pharmaceutical preparation containing as a medicament insulin which in oral administration is said to lose its pharmaceutical effect as a result of being decomposed by proteases in the digestive tract, and administered these tablets to the sublingual mucosa of a rat. As compared with a blank not containing this medicament, the rat administered with the insulin-containing tablets exhibited abnormal behaviors with hairs erect and trembling. This led to the presumption that insulin was absorbed through the sublingual or buccal mucosa, and the rat was in a hypoglycemic condition.

(3) The pharmaceutical preparation of this invention does not dissolve and flow out even upon the absorption of the saliva or secretions. In the swollen state, the preparation still retains a form similar to the original form, and has good form retention, and moreover, it is not sticky. Accordingly, it scarcely presents a feeling of the presence of foreign matter, and the patient can endure impulse to touching the preparation with the tongue or peeling it off. With a certain medicament, necessity may arise to stop administration urgently so as to avoid danger. In such an event, the pharamceutical preparation of the invention can be removed easily by pincers of fingers, or by washing.

(4) The rate of releasing the medicament can be controlled easily to suit the purpose of therapy by changing the ratio between the cellulose ether and the acrylic homo- or copolymer or its pharmaceutically acceptable salt within the specified range.

(5) The procedure of preparing the pharmaceutical preparation of this invention is easy, and its molding can be performed by press-forming. This molding method is advantageous because it does not impair the stability of the medicament, and is economical. The preparation can be molded into various forms such as granules and powders.

The following Examples illustrate the present invention in greater detail. It should be understood however that the invention is in no way limited to these specific examples.

EXAMPLE 1

This Example is given to make it clear that the polymeric matrix composed of a cellulose ether and an acrylic polymer or copolymer does not show much solubility, and has superior swellability, form retention and mucosa adhesiveness with reduced irritation to the mucosa.

(A) Fine powders of the cellulose ethers and polyacrylic acid shown in Table 1 in the amounts indicated were thoroughly mixed in a mixer, and magnesium stearate was added in an amount of 0.5% based on the total weight of the mixture. Discs having a weight of about 90 mg, a thickness of about 2 mm, a diameter of 7 mm and a Monsanto hardness of about 5 to 20 kg were prepared from the resulting intimate mixture.

Each of the discs was placed stood on agar gel at 37° C., and changes in the diameter and weight of the disc as a measure for its swellability were observed, and changes in the form of the disc and its flowability were observed as a measure for form retention. The results are shown in Table 1.

(B) Two rubber sheets each lines with a steel sheet equipped with a hook were wetted a small amount of water, and then each of the discs prepared in (A) was interposed between them. A load of 100 g was exerted for 30 seconds to bond the disc to the rubber plates. Then, water was filled in the space between the rubber sheets. One hook was fixed, and a load was exerted on the other hook. The load which is caused the peeling of the disc from the rubber sheets was measured, and made the adhesion strength of the disc in a wet condition. The results are shown in Table 2.

As controls, discs prepared from hydroxypropyl cellulost alone, polyacrylic acid alone, and a 1:1 mixture of polyacrylic acid sodium salt and lactose in the same way as above were tested in the same way as above. The results are also shown in Tables 1 and 2.

(C) Discs prepared in the same way as above and having a weight of about 40 mg, a thickness of about 1.1 mm, a diameter of 7 mm and a Monsanto hardness of about 5 to 6 kg were applied to the mucous membranes on the inner sides of the lower lips of five human subjects (A, B, C, D, and E), respectively. After a lapse of 4 hours, the discs were peeled off. Five minutes later, the condition of the surface of the mucosa to which the disc had been applied was visually observed. The results are shown in Table 3.

TABLE 1

| Standing time (hours) | Weight ratio of hydroxypropyl cellulose (*2)/polyacrylic acid (*3) | | | | | | | | | | | | | | | | | |
|---|---|---|---|---|---|---|---|---|---|---|---|---|---|---|---|---|---|---|
| | 95/5 | | | 90/10 | | | 75/25 | | | 65/35 | | | 50/50 | | | 25/75 | | |
| | D (*1) | W (*1) | F (*1) | D | W | F | D | W | F | D | W | F | D | W | F | D | W | F |
| 1 | 10.2 | — | Good | 10.1 | — | Good | 12.2 | — | Good | 14.5 | — | Good | 13.2 | — | Good | 18.5 | — | Good |
| 3 | 14.3 | — | " | 16.4 | — | " | 19.0 | — | " | 22.3 | — | " | 27.6 | — | " | 27.6 | — | " |
| 6 | 25.0 | 80.2 | " | 23.5 | 68.0 | " | 25.2 | 91.9 | " | 30.5 | 98.0 | " | 35.3 | 93.1 | " | 32.3 | 200 | " |
| 10 | 28.7 | — | " | 29.7 | — | " | 31.4 | — | " | 36.5 | — | " | 37.2 | — | " | 40.5 | — | " |
| 22 | 37.8 | 155 | " | 38.6 | 168 | " | 43.9 | 190 | " | 45.5 | 170 | " | 47.9 | 195 | " | 60.1 | 403 | " |
| 52 | 44.3 | 250 | " | 53.8 | 232 | " | 60.2 | 265 | " | 57.0 | 242 | " | 56.1 | 254 | " | 75.5 | 513 | " |
| 76 | 54.5 | 261 | " | 62.5 | 262 | " | 70.3 | 281 | " | 69.0 | 286 | " | 59.0 | 292 | " | 86.1 | 649 | " |

| Standing time (hours) | Weight ratio of methyl cellulose (*4)/polyacrylic acid (*3) | | | Weight ratio of hydroxyethyl cellulose (*5)/polyacrylic acid (*3) | | | Weight ratio of hydroxypropylmethyl cellulose (*6)/polyacrylic acid (*3) | | | Hydroxypropyl cellulose (*2) | | | Polyacrylic acid (*3) | | | Weight ratio of pply-sodium acrylate (*7)/lactose | | |
|---|---|---|---|---|---|---|---|---|---|---|---|---|---|---|---|---|---|---|
| | 85/15 | | | 75/25 | | | 85/15 | | | | | | | | | 50/50 | | |
| | D | W | F | D | W | F | D | W | F | D | W | F | D | W | F | D | W | F |
| 1 | 12.1 | — | Good | 14.0 | — | Good | 10.2 | — | Good | 9.4 | — | Partly dissolved | 39.6 | — | Good | 36.6 | — | Partly dissolved |
| 3 | 18.8 | — | " | 21.0 | — | " | 15.1 | — | " | 13.7 | — | Partly dissolved | 48.9 | — | " | 55.4 | — | Partly dissolved |
| 6 | 23.6 | 98.0 | " | 30.5 | 162 | " | 21.6 | 89.2 | " | 28.5 | — | Became flowable | 57.6 | 251 | " | 74.1 | — | Became flowable |
| 10 | 30.8 | — | " | 37.2 | — | " | 30.2 | — | " | — | — | Became flowable | 59.7 | — | " | — | — | Became flowable |
| 22 | 40.2 | 183 | " | 48.0 | 241 | " | 38.1 | 172 | " | — | — | Became flowable | 74.1 | 565 | " | — | — | Became flowable |
| 52 | 63.3 | 283 | " | 61.2 | 358 | " | 55.3 | 296 | " | — | — | Became flowable | 88.5 | 758 | " | — | — | Became flowable |
| 76 | — | — | — | — | — | — | — | — | — | — | — | Became flowable | 97.8 | 1006 | " | — | — | Became flowable |

TABLE 2

| Weight ratio of hydroxypropyl cellulose/polyacrylic acid | 100/0 | 95/5 | 90/10 | 85/15 | 75/25 | 65/35 | 50/50 | 25/75 | 10/90 | 0/100 |
|---|---|---|---|---|---|---|---|---|---|---|
| Adhesion strength (g/cm²) | 230 | 300 | 350 | 400 | 490 | 690 | 1290 | 1810 | 1750 | 1660 |

TABLE 3

| Condition of the mucosa | Subjects | Weight ratio of hydroxypropyl cellulose/polyacrylic acid | | | | | | |
|---|---|---|---|---|---|---|---|---|
| | | 95/5 | 90/10 | 75/25 | 65/35 | 50/50 | 25/75 | 10/90 |
| Whitening of the mucosa | A | — | — | — | ± | ± | ++ | ++ |
| | B | — | — | — | ± | ± | + | ++ |
| | C | ± | ± | ± | ± | ± | ++ | ++ |
| | D | — | — | — | — | ± | + | + |
| | E | — | — | — | ± | ± | + | ++ |

TABLE 3-continued

| Condition of the mucosa | Subjects | Weight ratio of hydroxypropyl cellulose/ polyacrylic acid | | | | | | |
|---|---|---|---|---|---|---|---|---|
| | | 95/5 | 90/10 | 75/25 | 65/35 | 50/50 | 25/75 | 10/90 |
| | A | − | − | − | ± | ± | + | + |
| Occurrence | B | − | − | − | − | − | + | + |
| of blister -like | C | − | ± | ± | ± | ± | + | + |
| protru- | D | − | − | − | − | − | ± | +μ |
| sions | E | − | − | − | − | − | + | + |

The evaluations were made on the following scale.
−: quite normal
±: almost normal
+: abnormal
++: quite abnormal It is seen from Table 1 that the discs made from the mixture of cellulose ether and polyacrylic acid and from polyacrylic acid alone swell continuously, but do not become flowable and well retain the form similar to the original discs, and therefore that these discs are suitable as a matrix for use in adhesion of pharmaceutical preparations to the mucosa of the oral or nasal cavity. In contrast, the matrix composed of the cellulose ether alone and the matrix composed of a 1:1 mixture of the cellulose ether and polysodium acrylate immediately began to dissolve partly on agar gel, and became flowable within a short period of time. Hence, these matrices are useless for adhesion to the mucosa of the oral or nasal cavity. It is also clear from Table 2 that the matrix composed only of the cellulose ether does not have a sufficient adhesion strength. In a clinical test, this matrix immediately peels from the muscosa of the oral cavity, and is therefore useless. As shown in Table 2, the matrix composed of the cellulose ether and polyacrylic acid has a stronger adhesion strength as the proportion of the polyacrylic acid is larger.

It can be concluded from the results given in Table 1 and 2 that a matrix composed of the cellulose ester and polyacrylic acid (or its sodium salt) is suitable for adhesion to the mucosa of the oral or nasal cavity, and its adhesion strength is higher with increasing proportion of the polyacrylic acid (or its salt). On the other hand, as is clear from the results of the clinical tests shown in Table 3, the irritation of the matrix to the mucosa of the oral cavity becomes stronger when the proportion of the polyacrylic acid in the mixed matrix exceeds 50%, and depending upon the physical condition of the subject, serious inflammation may be caused, and therefore, such matrix is unsuitable for adhesion to the mucosa of the oral or nasal cavity. This fact indicates that the pharmaceutical preparation composed of an anticancer agent and a polymeric mixture of hydroxypropyl cellulose and polyacrylic acid for intraperitoneal or uterine application which is disclosed in Japanese Laid-Open Patent Publication cannot be directly applied to the pharmaceutical preparations of this invention which are adhesive to the mucosa of the oral or nasal cavity.

It is seen from the results shown in Table 1, 2 and 3 that a mixture of 50 to 95% by weight of a cellulose ether and 50 to 5% by weight of polyacrylic acid (or its pharmaceutically acceptable salt) is very suitable as a matrix for pharmaceutical preparations which are used adhering to the mucosa of the oral or nasal cavity.

EXAMPLE 2

This Example shows that the medicament is released gradually at a controlled rate from the pharmaceutical preparation of this invention.

(A) Predetermined amounts of the cellulose ethers and polyacrylic acid shown in Table 4, and 4 mg (per tablet which weighed about 200 mg) of a dye (amaranth) were thoroughly mixed in a mixer. Then, 1 mg of magnesium stearate was lightly mixed. Discs having a weight of about 200 mg, a thickness of about 1.4 mm and a diameter of 10.0 mm were press-formed from the resulting intimate mixture. The discs were placed on agar gel at 27° C., and the amount of the dye which was released into the agar with time was determined by measuring the absorbance at 520 mμ. The release rate (%) of the dye was thus measured. The results are shown in Table 4.

For comparison, discs were prepared in the same way as above using sucrose and lactose, and subjected to the same test as above. The results are also shown in Table 4.

TABLE 4

| Standing time (hours) | Weight ratio of hydroxypropyl cellulose/ polyacrylic acid | | | | Weight ratio of methyl cellulose/ polyacrylic acid | Weight ratio of hydroxyethyl cellulose/ polyacrylic acid | Weight ratio of hydroxypropylmethyl cellulose/ polyacrylic acid | Sucrose | Lactose |
|---|---|---|---|---|---|---|---|---|---|
| | 90/10 | 75/25 | 65/35 | 50/50 | 85/15 | 85/15 | 85/15 | | |
| 6 | 22.5 | 24.1 | 22.0 | 21.6 | 23.9 | 28.9 | 22.8 | 100 | 75.0 |
| 30 | 72.0 | 70.1 | 70.2 | 69.0 | 72.8 | 78.2 | 74.2 | — | 100 |
| 48 | 74.9 | 74.1 | 74.5 | 72.0 | 75.1 | 84.3 | 78.3 | — | — |
| 96 | 82.2 | 81.9 | 80.3 | 81.1 | 84.4 | — | 86.2 | — | — |

It is clearly seen from the results given in Table 4 that the releasing of the dye was much slower in teh pharmaceutical preparations of this invention than in the discs containing sucrose and lactose which correspond to ordinary troches.

(B) The discs in accordance with this invention obtained in (A) above were pressed against a slightly water-wetted plastic auxiliary plate and fixed in position. The plate was shaken in water at 37° C. in accordance with the method of a disintegration test set forth in the 9th Revised Edition of Japanese Pharmacopoeia. The amount of the dye released into water was determined by measuring the absorbance at 520 mµ. Thus, the release rate (%) of the dye was calculated. The results are shown in Table 5.

For comparison, tablets composed of 150 parts of crystalline cellulose, 46 parts of carboxymethyl cellulose calcium salt, 4 parts of amaranth and 1 part of magnesium stearate, and tablets composed of 100 parts of crystalline cellulose, 71 parts of lactose, 25 parts of carboxylmethyl cellulose calcium, 4 parts of amaranth and 1 part of magnesium stearate were prepared in the same way as above by a direct tableting method. The tablets were fixed to a plastic auxiliary plate using a small amount of an adhesive, and tested in the same way as above. The results are also shown in Table 5.

TABLE 5

| Shaking time (minutes) | Composition | | |
|---|---|---|---|
| | Hydroxypropyl cellulose/ polyacrylic acid (3:1) | Crystalline cellulose + calcium carboxy methyl cellulose | Crystalline cellulose + lactose + carboxymethyl cellulose calcium |
| 20 | 15.1 | 100 | 100 |
| 70 | 28.3 | — | — |
| 120 | 35.3 | — | — |
| 180 | 45.1 | — | — |
| 240 | 54.6 | — | — |

It is seen from the results given in Table 5 that the pharmaceutical preparation of this invention releases the dye into water more slowly at a substantially fixed rate than the tablets obtained by the direct tableting method.

(C) One hundred milligrams of granules or powders (having the particle diameters shown in Table 6) were prepared from the discs composed of a 3:1 mixture of hydroxypropyl cellulose and polyacrylic acid in (A) above were placed on agar gel in a circular shape having a diameter of 17 mm, and the release rate (%) of the dye was measured. The results are shown in Table 6.

TABLE 6

| Standing time (hours) | Particle diameter (mesh) | | |
|---|---|---|---|
| | 20–32 | 32–60 | Smaller than 60 |
| 10 | 83.6 | 85.2 | 88.6 |
| 28 | 94.2 | 96.3 | 97.5 |
| 48 | 96.9 | 98.1 | 98.6 |

It is seen from the results shown in Table 6 that granules and powders have a faster rate of release than discs, and the rate of release increases with decreasing particle diameter.

EXAMPLE 3

(3-1) 85 Parts of hydroxypropyl cellulose having a viscosity, determined at 20° C. for its 2.0% aqueous solution, of 2080 centipoises and a particle diameter smaller than 60 mesh, 15 parts of an acrylic acid copolymer (Carbopol 934, a product of B. F. Goodrich Chemical Co., composed mainly of acrylic acid and allyl sucrose), and 0.125 part of triamcinolone acetonide, an anti-inflammatory steroid were well mixed in a mixer. Then, 0.5 part of magnesium stearate was added and mixed lightly to form a powder for tablet formation. The powder was directly tableted to obtain tablets each having a diameter of 7 mm, a thickness of 1.1 mm, a weight of 40 mg and a Monsanto hardness of 5.6 kg and containing 50 µg of triamcinolone acetonide which were adhesive to the mucosa of the oral cavity and intended for the treatment of oral aphthosis.

(3-2) The tablets obtained in (3-1) were adhered to that area of the mucosa of the oral cavity at which aphthosis occurred in 15 human subjects with recurrent stomatic aphthosis. When the administration was effected two times daily (one tablet for each time), eleven subjects got their inflammation relieved by one to two administrations, and the remaining four got their inflammation relieved by 3 to 4 administrations.

On the other hand, a marketed oral ointment containing triamcinolone acetonide (concentration 0.1% by weight of the active ingredient) was applied to the stomatic lesion of 15 subjects two times daily in a dose of about 50 mg per subject for each time. Ten subjects got their inflammation relieved by 6 to 7 applications, and the remaining five subjects got their inflammation relieved after 8 to 10 applications.

In applying the ointment, the subjects felt a keen pain, whereas in applying the pharmaceutical preparation in accordance with this invention, no pain was caused to the subjects. Furthermore, in the application of ointment, depending upon the site of aphtha, the ointment applied peeled off in 10 to 40 minutes and was either swallowed or disappeared. In contrast, the preparation in accordance with this invention adhered to the lesion for 3 to 6 hours, and continuously released the medicament. Hence, the method of administration in accordance with this invention is very good.

EXAMPLE 4

(4-1) A tableting powder obtained in the same way as in Example 3 was filled in hard gelatin capsules, and capsules were obtained each of which had a weight of 160 mg and contained 20 µg of triamcinolone acetonide. These capsules are placed in a spray vessel, and prior to use, small holes are formed in the capsules and the air is sent through the holes to spray the powder onto the mucosa of the oral or nasal cavity.

(4-2) The capsules containing triamcinolone acetonide prepared in (4-1) were placed in a sprayer equipped with needles and a rubber ball for sending the air, and applied to five human subjects with allergic rhinitis. Prior to use, the needles were caused to penetrate through the capsules to form small holes, and then the tip of the sprayer was inserted into the nasal cavity. The rubber ball was pushed to send the air, and to spray the powder from the tip of the sprayer, thus causing it to adhere to the mucosa of the nasal cavity. As a result, sneezing rapidly subsided, and the feeling of nasal closure was removed. By one spraying operation, the effect of the medicament lasted for more than several hours.

For comparison, an anti-inflammatory steroid in solution was dropped into the nasal cavity. But the solution flowed into the throat, and the effect of the medicament was insufficient. Its effect lasted only for less than several hours.

EXAMPLE 5

(5-1) 75 Parts of hydroxypropyl cellulose having a viscosity, determined at 20° C. for its 2.0% aqueous solution, of 6.0 centipoises, 25 parts of an acrylic acid copolymer (Carbopol 934), 0.5 part of magnesium stearate and 1.8 parts of indomethacin as an anti-inflammatory agent were mixed thoroughly to form an intimate powder mixing for tableting. By using an ordinary tableting machine, tablets adhesive to the mucosa of the oral cavity were obtained each of which had a weight of 22.7 mg and a diameter of about 5 mm.

(5-2) Five SD rats (males, body weight 190 to 200 g) were used for each of the measuring times employed. The tablet prepared in (5-1) above was adhered and fixed to the sublingual mucosa under ether anaesthesia to administer indomethacin in a dose of 0.4 mg/head. The rats were shackled to prevent removal of the tablets by the legs. About 5 ml of the blood was sampled at 30 minutes, 1 hour 2 hours, 3 hours, 4 hours, 6 hours, 8 hours, and 12 hours after the administration, and the concentration of indomethacin in the blood was measured. The blood taken before the testing was used as a control.

The determination of the indomethacin level in the plasma was performed by a method which conformed substantially to the method disclosed in L. P. J. Holt, et al. (Brit. Med. J., 1,1354 (1965)). Specifically, a 0.1 M phosphate buffer and 0.5 M citrate buffer were added to the plasma obtained from the blood to adjust the pH to about 5.0. The solution was extracted with n-heptane, and a 0.1 N sodium hydroxide solution was added, and the mixture was shaken. The aqueous layer was taken, heated at 50° C. for 30 minutes, cooled with ice, and allowed to stand at room temperature for 5 minutes. The fluorescence intensity of the solution at a fluorescence wavelength of 375 m$\mu$ and an excitation wavelength of 295 m$\mu$ was measured by a fluorescence spectrometer (Hitachi, MPF 4) to determine the concentration of indomethacin in the blood. The results are shown in FIG. 1. Each point in FIG. 1 was the average of the concentrations of indomethacin in the plasma of five rats. On the other hand, for comparison, a fine powder of indomethacin and a 5% solution of gum arabic powder were ground in a mortar. The suspension of indomethacin was orally administered in a dose of 0.4 mg/head as indomethacin to SD rats (male, body weight 190 to 200 g) using a tube. The concentration of indomethacin in the plasma was measured. The results are also shown in FIG. 1.

In FIG. 1, the ordinates represents the indomethacin level in the plasma of rat ($\mu$g/ml), and the abscissa, the time (hours) which elapsed after the administration of the pharmaceutical preparation of this invention and the indomethacin suspension, respectively. The curve a refers to an absorption curve obtained when the indomethacin suspension was orally administered (control), and the curve b refers to an absorption curve obtained by applying the pharmaceutical composition prepared in (5-1) above.

It is seen from FIG. 1 that according to the administering method of this invention the absorption of indomethacin in the blood is continuous, and the effect of the medicament lasts over a longer period of time.

It is known that indomethacin shows a strong side-effect of gastric disorder when orally administered. The administering method of this invention can markedly reduce this side-effect. This will be clarified by the following comparative experiment.

75 Parts of hydroxypropyl cellulose, 25 parts of an acrylic acid copolymer, 0.5 part of magnesium stearate and 18 parts of indomethacin, an anti-inflammatory agent, were mixed intimately to form a powder mixture for tableting. By using an ordinary tableting machine, tablets were prepared from the powder mixture which were adhesive to the mucous membrane and each of which had a weight of 26.3 mg and a diameter of 5 mm and contained 4 mg of indomethacin.

The tablet was adhered and fixed to the sublingual mucosa of SD rats (male, body weight 190-200 g, five per group) which had been fasted for 24 hours while being allowed to take water freely. The rats were shackled to prevent removal of the tablets by the legs.

Seven hours after the administration of the medicament, a 5% Evans blue solution was intravenously injected into the rats in an amount of 0.4 to 0.5 ml/head to stain the tissues, and 10 minutes after the vital stain, the whole blood was taken under anaesthesia. The animals were killed, and the stomach was taken out. 15 ml of a 1% formaldehyde solution was injected into the stomach, and the stomach was fixed in position in a 1% formaldehyde solution. After fixation, the stomach was incised along the greater curvature, and the number of ulcers which were generated on the gastric mucosa was measured and made an ulcer index.

The above procedure was repeated except that a 5% gum arabic solution of indomethacin was orally administered.

The results are shown in Table 7.

TABLE 7

| Sample | Dose (mg/head) | Ulcer index (number) | Incidence |
|---|---|---|---|
| Pharmaceutical preparation of this invention | 4 | 16.8 ± 2.6* | 5/5 |
| 5% gum arabic powder solution of indomethacin | 4 | 32.2 ± 2.7 | 5/5 |

*significant at t (8, 0.05)

EXAMPLE 6

Predetermined amounts of the same hydroxypropyl cellulose and acrylic acid copolymer (Carbopol 934) as used in Example 3, and 50 mg, for each disc weighing about 450 mg, of isoproterenol hydrochloride (antiasthma agent) were fully mixed in a mixer. Furthermore, 2 mg of magnesium stearate was added. The resulting intimate mixture was molded into discs each having a thickness of 3 mm and a diameter of 10 mm.

The discs was placed on agar gel at 37' C. and changes in the diameter and weight of the discs and the releasability of the medicament were measured. The releasability of the medicament was determined by determining the $\mu$ amount of the medicament released into the agar with time from the measurement of the absorbance at 279 m$\mu$. The increase (times) of the diameter of the disc is shown in Table 8, and the increase (times) of the weight of the disc is shown in Table 9. The release rate (%) of the medicament from the disc to the agar gel is shown in Table 10.

TABLE 8

| Standing time (hours) | Weight ratio of hydroxypropyl cellulose/ acrylic acid copolymer | |
|---|---|---|
| | 3/1 | 1/1 |
| 6 | 1.48 | 1.52 |
| 24 | 1.58 | 1.54 |
| 48 | 1.67 | 1.60 |
| 72 | 1.71 | 1.62 |
| 96 | 1.76 | 1.69 |

TABLE 9

| Standing time (hours) | Weight ratio of hydroxypropyl cellulose/ acrylic acid copolymer | |
|---|---|---|
| | 3/1 | 1/1 |
| 6 | 1.40 | 1.6 |
| 24 | 2.03 | 1.98 |
| 48 | 2.21 | 2.08 |
| 72 | 2.45 | 2.12 |
| 96 | 2.68 | 2.17 |

TABLE 10

| Standing time (hours) | Weight ratio of hydroxypropyl cellulose/ acrylic acid copolymer | |
|---|---|---|
| | 3/1 | 1/1 |
| 6 | 21.0 | 19.2 |
| 24 | 43.6 | 42.6 |
| 48 | 66.3 | 57.8 |
| 72 | 74.2 | 67.0 |
| 96 | 78.5 | 70.2 |

It is seen from Tables 8 and 9 that the pharmaceutical preparations of this invention have very good form retention, swelling to a form symmetrical to the original discs.

The results given in Table 10 demonstrate that the pharmaceutical preparations of this invention are slow releasing, and the release rate of isoproterenol hydrochloride into agar was higher with larger proportion of hydroxypropyl cellulose.

EXAMPLE 7

Predetermined amounts of the same hydroxypropyl cellulose and acrylic acid copolymer (Carbopol 934) as used in Example 3, and 10 mg. for each disc having a weight of about 410 mg, of benzocaine (local anaesthetic) were fully mixed in a mixer, and 2 mg of magnesium stearate was added. Discs each having a thickness of 25 mm and a diameter of 10 mm were prepared by press-forming the resulting mixture. The discs were placed stationary on agar gel at 37° C., and changes in the diameter and weight of the discs and the releasability of benzocaine were observed.

The releasability of benzocaine was determined by determining the amount of medicament released into the agar gel with time from the measurement of the absorbance at 284 mμ.

The increase (times) of the disc is shown in Table 11, and the increase (times) in the weight of the disc is shown in Table 12. The release rate (%) of benzocaine from the disc to the agar gel is shown in Table 13.

TABLE 11

| Standing time (hours) | Weight ratio of hydroxypropyl cellulose/ acrylic acid copolymer | |
|---|---|---|
| | 3/1 | 1/1 |
| 24 | 1.88 | 1.85 |
| 48 | 2.02 | 1.96 |
| 72 | 2.12 | 2.01 |
| 96 | 2.13 | 2.17 |

TABLE 12

| Standing time (hours) | Weight ratio of hydroxypropyl cellulose/ acrylic acid copolymer | |
|---|---|---|
| | 3/1 | 1/1 |
| 24 | 3.02 | 3.03 |
| 48 | 3.78 | 3.80 |
| 72 | 4.20 | 4.21 |
| 96 | 4.60 | 4.75 |

TABLE 13

| Standing time (hours) | Weight ratio of hydroxypropyl cellulose/ acrylic acid copolymer | |
|---|---|---|
| | 3/1 | 1/1 |
| 24 | 11.8 | 9.1 |
| 48 | 18.2 | 12.5 |
| 72 | 24.0 | 17.2 |
| 96 | 31.4 | 19.8 |

As is clearly seen from Tables 11 and 12, both the diameters and weights of the discs increased with time. The diameter tended to increase with increasing proportion of hydroxypropyl cellulose, but the weight is not affected by this factor.

The swollen discs of this invention had a shape symmetrical to the original discs, showing very good form retention.

The results shown in Table 13 demonstrate that the amount of benzocaine released into the agar gel increased almost linearly over a long period of time, and the benzocaine release speed was higher with larger proportion of hydroxypropyl cellulose.

EXAMPLE 8

Discs each having a thickness of 1.4 mm and a diameter of 10.0 mm were prepared in the same way as in Example 6 except that 2 mg, for each disc having a weight of about 200 mg, of triamcinolone acetonide (anti-inflammatory agent) was used instead of the isoproterenol hydrochloride in Example 6.

The discs were pressed against a slightly water-wetted glass surface and fixed there, and dipped in a 1:1 mixture of water and ethanol. The amount of triamcinolone acetonide which was released into the solution with time was determined by measuring the absorbance of the solution at 239 mμ.

The results are shown in FIG. 2 of the accompanying drawings. The ordinate represents the release rate (%) of triamcinolone acetonide, and the abscissa represents the dipping time (hours). Curves c, d, e and f refer to curves obtained with the hydroxypropyl cellulose/acrylic acid copolymer in a weight ratio of 9:1, 3:1, 1:1, and 1:3, respectively. It is seen from FIG. 2 that triamcinolone acetonide was released linearly with time, and the speed of release increases with increasing proportion of hydroxypropyl cellulose.

EXAMPLE 9

Discs each having a thickness of 1.4 mm and a diameter of 10.0 mm were prepared in the same way as in Example 6 except that 18 mg, for each disc weighing about 220 mg, of tetracycline hydrochloride (antibacterial agent) was used instead of the isoproterenol hydrochloride in Example 6.

These discs were pressed against a slightly water-wetted plastic auxiliary plate and fixed there. By the method of testing disintegration in accordance with Japanese Pharmaceopoeia, the plate was shaken in water at 37° C. The amount of the tetracycline hydrochloride released into water was determined by measuring the absorbance of the solution at 355 mμ.

The results are shown in FIG. 3 of the accompanying drawings. Troches (containing tetracycline hydrochloride in a concentration of 15 mg per tablet) made by Japan Lederle Co., Ltd. were also tested in the same way as above, and the results are also shown in FIG. 3.

In FIG. 3, the ordinate represents the release rate (%) of etetracycline hydrochloride, and the abscissa represents the shaking time (hours). Lines g, h, i and j refer to the hydroxypropyl cellulose/acrylic acid copolymer mixture in a weight ratio of 9:1, 3:1, 1:1, and 1:3, respectively. Line k refers to a curve obtained with the trouches. It was seen from FIG. 3 that the pharmaceutical preparations of this invention are slow-releasing, and the speed of releasing varies depending upon the ratio between the hydroxypropopyl cellulose and the acrylic acid copolymer. Curves g and h showed almost the same speeds of release.

EXAMPLE 10

(10-1) Mucosa-adhesive tablets composed of 85 parts of methyl cellulose having a viscosity, determined at 20° C. for its 2% aqueous solution, of 1335 centipoises, 15 parts of acrylic acid copolymer (Carbopol 934) and 0.25 mg, per tablet, of dequalinium chloride, an oral antiseptic and each having a weight of 40 mg were prepared, and administered to 12 human subjects complaining of swelling and pain at the throat by adhering them to the palate. Although depending upon the site of adhering, the tablets were kept adhering to the palate for 2 to 3 hours, and most of the subjects reported to alleviation or curving of the swelling and pain within this period.

(10-2) Marketed troches containing dequalinium chloride were administered to 10 human subjects complaining of almost the same condition. In most of them, the troches dissolved away in about 10 minutes, and to alleviate the swelling and pain, it was usually necessary to take 6 to 8 troches in the mouth continuously. In addition, the effect of the troches scarcely lasted and in 1 to 2 hours, many of the subjects again complained of swelling and pain at the throat.

What we claim is:

1. In a method for administering a medicament which comprises adhering with a polyacrylate to the mucosa of the oral cavity a pharmaceutical preparation, the improvement comprising adhering said medicament with (a) a water-swellable and mucosa-adhesive polymeric matrix comprising about 50 to about 95% by weight of a cellulose ether and about 50 to about 5% by weight of a homo- or copolymer of acrylic acid or pharmaceutically acceptable salt thereof, and (b) dispersed therein, a pharmaceutically effective amount of the medicament to be adhered to the oral mucosa, said preparation releasing continuously the medicament at a controlled rate; and causing the released medicament to be absorbed through the mucosa or enterally.

2. The method of claim 1 wherein said polymeric matrix comprises about 65 to about 90% by weight of the cellulose ether and about 35 to about 10% by weight of the homo- or copolymer of acrylic acid or its pharmaceutically acceptable salt.

3. The method of claim 1 wherein the cellulose ether is a lower alkyl or hydroxy lower alkyl ether of cellulose.

4. The method of claim 1 wherein the cellulose ether is selected from the group consisting of methyl cellulose, hydroxyethyl cellulose, hydroxypropylmethyl cellulose and hydroxypropyl cellulose.

5. The method of claim 1 wherein the cellulose ether is hydroxypropyl cellulose having a viscosity, determined at 20° C. for a 2% by weight aqueous solution thereof, of 3 to 10,000 centipoises.

6. The method of claim 1 wherein the polymer of acrylic acid has a viscosity of 360 to 165,000 centipoises when it is measured at 25.0±5° C. for an aqueous solution of the sodium salt of the polymer having a pH of 7 to 7.5 and a concentration of 0.2% by weight as free polymer.

7. The method of claim 1 wherein the pharmaceutical preparation further comprises an excipient dispersed in the matrix.

8. The method of claim 1 wherein the medicament is selected from the group consisting of analgesic and anti-inflammatory agents, anti-inflammatory enzyme preparations, anti-inflammatory steroids, antihistamines, antibiotics, antibacterial agents, chemotherapeutic agents, local anaesthesias, cardiac tonics, vasodilators, antitussive and expectorants, oral antiseptics, enzyme proteins, hypoglycemic agents, hemostats, hormones, hypotensive agents, sedatives or tranquilizers, anti-tumor agents, gastro intestinal drugs and antacids.

9. The method of claim 1 wherein the pharmaceutical preparation is in the form of tablets, granules, fine granules, powders and dental cone.

* * * * *